United States Patent
Yamashita et al.

(10) Patent No.: US 7,135,327 B2
(45) Date of Patent: Nov. 14, 2006

(54) RIBONUCLEIC ACID-ENRICHED BREWER'S YEAST CELLS AND PROCESS FOR PRODUCING THE SAME

(75) Inventors: Shinji Yamashita, Yaizu (JP); Hisao Kado, Shibuya-ku (JP); Taiju Masuda, Yaizu (JP)

(73) Assignee: Sapporo Breweries Limited, Tokyo (JP)

( * ) Notice: Subject to any disclaimer, the term of this patent is extended or adjusted under 35 U.S.C. 154(b) by 46 days.

(21) Appl. No.: 10/472,032

(22) PCT Filed: Mar. 13, 2002

(86) PCT No.: PCT/JP02/02369

§ 371 (c)(1),
(2), (4) Date: Mar. 3, 2004

(87) PCT Pub. No.: WO02/074933

PCT Pub. Date: Sep. 26, 2002

(65) Prior Publication Data

US 2004/0142457 A1 Jul. 22, 2004

(30) Foreign Application Priority Data

Mar. 19, 2001 (JP) ............................ P2001-078675

(51) Int. Cl.
*C12N 1/18* (2006.01)
(52) U.S. Cl. ................................... 435/255.2
(58) Field of Classification Search ............. 435/255.2
See application file for complete search history.

(56) References Cited

U.S. PATENT DOCUMENTS 3,272,714 A  9/1966 Watanabe et al.
3,909,352 A  9/1975 Akiyama et al.
4,330,464 A * 5/1982 Lawford et al. ............ 530/416

FOREIGN PATENT DOCUMENTS

| | | | |
|---|---|---|---|
| DE | 4004633 | * | 8/1991 |
| JP | 52-90684 | | 7/1977 |
| JP | 53-118584 | | 10/1978 |
| JP | 54-49395 | | 4/1979 |
| JP | 60-141283 | | 7/1985 |
| JP | 5-176757 | | 7/1993 |
| JP | 11-196859 | | 7/1999 |

OTHER PUBLICATIONS

Walter C. Schneider, J.Biol.Chem. vol. 164, p. 747 1946.
Patent Abstracts of Japan, JP 5-176757, Jul. 20, 1993 (with cover page only).
Patent Abstracts of Japan, JP 60-141283, Jul. 26, 1985 (with cover page only).
Derwent Publications, AN 1966-09871, XP-002282470, JP 38-023088, 1963.

* cited by examiner

*Primary Examiner*—Herbert J. Lilling
(74) *Attorney, Agent, or Firm*—Oblon, Spivak, McClelland, Maier & Neustadt, P.C.

(57) ABSTRACT

By using a medium containing an ingredient for activating brewer's yeast, a brewer's yeast cell body is immersed in the medium in the presence of an added inorganic salt; and the immersion is stirred at a predetermined temperature to concurrently carry out an aerobic activation treatment, resulting in the formation of a brewer's yeast cell body containing a high ribonucleic acid content comprising 10% by weight or more of ribonucleic acid based on the weight of the cell body.

9 Claims, 2 Drawing Sheets

RIBONUCLEIC ACID-ENRICHED BREWER'S YEAST CELLS AND PROCESS FOR PRODUCING THE SAME

TECHNICAL FIELD

This invention relates to a brewer's yeast cell body containing high ribonucleic acid content and a method for its production.

BACKGROUND ART

Ribonucleic acid (RNA) is available as a raw material for a drug or a flavor enhancer such as 5'-inosinic acid (IMP) or 5'-guanylic acid (GMP). In general, the ribonucleic acid production employs yeast cell bodies that are cultured using waste molasses or liquid sugar as a major carbon source. Especially, yeasts are utilized for this purpose, *Candida utilis* and *Saccharomyces cerevisiae*. In an approach to increasing the ribonucleic acid content of yeast, attempts have been made, which include culturing in antibiotic-added media, the examination of major carbon sources and the isolation of mutant strains. Specifically, as U.S. Pat. No. 3,909,352 reports, a yeast of a Candida species is mutated, a strain having KCl susceptibility is then isolated, and a yeast cell body containing a ribonucleic acid content of 12% by weight or more in the solid mass (dried cell body) is thus produced. Further according to the publication of JP-A-11-196,859, a low temperature sensitive mutant is isolated from *Candida utilis* and a yeast cell body containing a ribonucleic acid content of 20% by weight or more in the solid mass is thus obtained.

Brewer's yeast that is used in brewing beer is washed after beer production; and its heat-dried cell bodies are utilized for the productions of dietary supplements and yeast extracts, and thus they are widely recognized as safe. Nevertheless, the yeast cell bodies recovered after beer production contain ribonucleic acid as much as at a level of about 4 to 6% in their solid masses; therefore, they have been considered as materials that are inadequate to extract ribonucleic acid on a commercial scale. Hence, studies of increased ribonucleic acid contents have been focused on *Candida* yeast species rather than on *Saccharomyces* yeast species, including bakers' yeast. The *Candida* yeast cell bodies, however, cannot necessarily be said to be non-toxic to the health of humans and animals and adequate precautions will be needed in the utilization of their products as foodstuff or feed additives. For this reason, there was proposed a method for increasing ribonucleic acid in a yeast cell body which uses a baker's yeast (Saccharomyces species of *Saccharomyces cerevisiae* DSM5616) under limitative fed-batch culture conditions (JP-A-05-176757). This method allowed a cell body having a ribonucleic acid content of 10% or more to be produced even when the solid mass exceeded 30 g/L. However, it was again only possible to attain the high ribonucleic acid content by limiting the strain for use in culturing as described above.

Thus, up till the present time there has not been known any brewer's yeast conventionally used having a ribonucleic acid content of 10% or more based on the weight of its cell body. Nor has there been an accomplished method for increasing the ribonucleic acid content of a brewer's yeast cell body to the aforementioned level.

Accordingly, this invention aims at providing a brewer's yeast cell body containing a high ribonucleic acid content comprising 10% by weight or more of ribonucleic acid based on the weight of the cell body; and it further aims at providing a method for efficiently producing such a brewer's yeast cell body without any restrictions of the strain to be used.

DISCLOSURE OF THE INVENTION

The present inventors made thorough investigations diligently in order to solve the above-stated problems, and consequently, discovered that an inorganic salt is allowed to act on a brewer's yeast cell body and activation treatment is performed on the cell body under specific conditions to produce a brewer's yeast cell body the ribonucleic acid content of which has been increased to 10% by weight or more. This has led to accomplishing the present invention.

Specifically, this invention provides a method for producing a brewer's yeast cell body containing a high ribonucleic acid content comprising 10% by weight or more of ribonucleic acid based on the weight of the cell body, the method comprising:

using a medium containing an ingredient for activating the brewer's yeast;

immersing the brewer's yeast cell body in the medium in the presence of an added inorganic salt; and stirring the immersion at a predetermined temperature to concurrently carry out aerobic activation treatment on the brewer's yeast cell body.

The invention also provides a brewer's yeast cell body containing a high ribonucleic acid content comprising 10% by weight or more of ribonucleic acid based on the weight of the cell body, the brewer's yeast cell body obtained by the aforementioned production method or other production methods.

The method for producing a brewer's yeast cell body containing a high ribonucleic acid content as described above can be characterized in that the inorganic salt is an inorganic salt of a metal selected from an alkali metal, an alkaline earth metal or a transition metal. Particularly, the inorganic salt is preferably sodium chloride.

In the method for producing a brewer's yeast cell body containing a high ribonucleic acid content as described above, the step of adding an inorganic salt to the immersion may be carried out at the start of the aerobic activation treatment. More preferably, the step of adding an inorganic salt to the immersion is carried out after the lapse of a predetermined period from the start of the aerobic activation treatment.

Further, the predetermined temperature is preferably in the range of from 10 to 30° C. in any of the methods for producing a brewer's yeast cell body containing a high ribonucleic acid content as described above.

In addition, according to the invention, there is provided a method for increasing the ribonucleic acid content of a brewer's yeast cell body, the method comprising:

using a medium containing an ingredient for activating the brewer's yeast;

immersing the brewer's yeast cell body in the medium in the presence of an added inorganic salt;

stirring the immersion at a predetermined temperature to concurrently carry out aerobic activation treatment on the brewer's yeast cell body; and producing ribonucleic acid in the brewer's yeast cell body at 10% by weight or more based on the weight of the cell body.

BEST MODE FOR CARRYING OUT THE INVENTION

Figure 1:
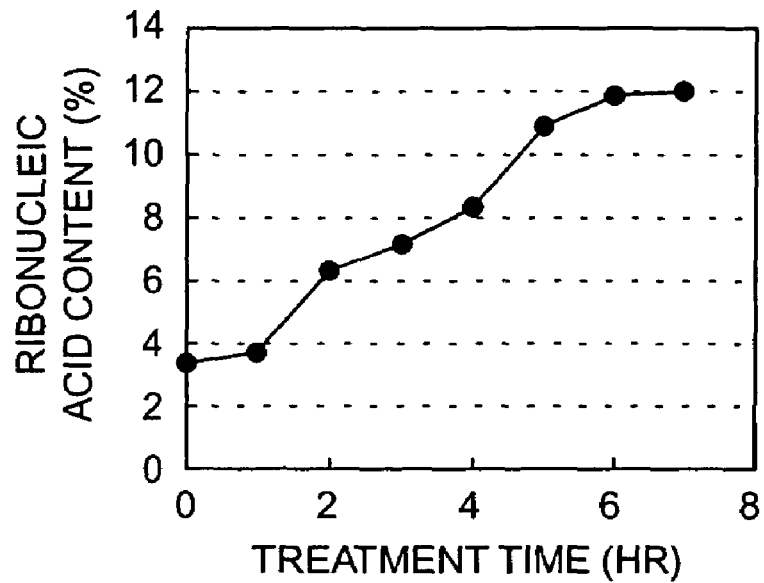
FIG. 1 is a graph showing the relationship between ribonucleic acid contents and brewer's yeast treatment time.

This invention will be described in detail hereafter.

The brewer's yeast cell body used in the invention may be yeast for use in conventional beer brewing.

The brewer's yeast cell body is first immersed in a medium containing an ingredient for activating the brewer's yeast.

A medium for use in culturing the yeast may be applied for the medium containing an ingredient for activating the brewer's yeast; but, the compositional ratio and the added amounts of nutrients should be controlled so that the growth of the yeast may not progress substantially. This is because ribonucleic acid that has previously been accumulated in the cell body is consumed during the growth phase of the yeast cell and the ribonucleic acid in the cell body deceases with the progression of growth. It is, therefore, necessary to take the following measures: for example, to at least impede the progression of growth so that the content of ribonucleic acid in the cell body may not be below 10% by weight as the result of the growth of the cells having progressed; and to confirm the period of when the content of ribonucleic acid reaches a peak by prior experimentation.

By the ingredient for activating the brewer's yeast is meant a carbon source, a nitrogen source, or any other ingredient, each of which is adjusted for its compositional ratio and its added amount in the medium. Suitable carbon sources include sugars (glucose, fructose, sucrose, maltose, oligosaccharide, waste molasses) and lipids. Suitable nitrogen sources include various ammonium salts (such as ammonium sulfate), urea, yeast extract, amino acids and beef extract. In addition, minerals, phosphoric acid or vitamins may appropriately be added to the medium, the addition of which is regarded as necessary for the yeast. The minerals include the salts of iron, cobalt, magnesium, calcium, zinc or copper.

The medium is used to prepare an immersion by immersing the brewer's yeast in the medium. While this immersion is stirred at a predetermined temperature in the presence of an added inorganic salt, the yeast is subjected to aerobic activation treatment. The inorganic salt to be added here promotes the activation of the brewer's yeast, i.e., ribonucleic acid production. An appropriate inorganic salt is an inorganic salt of a metal selected from an alkali metal (such as sodium or potassium), an alkaline earth metal (such as magnesium) or a transition metal (such as manganese). Among these inorganic salts, sodium chloride is most preferably used. The added amount of an inorganic salt is preferably in the range of from 0.5 to 2.0% by weight. The step of adding the inorganic salt to the immersion may be carried out at the start of the activation treatment. This includes adding the inorganic salt to the medium beforehand and causing the medium to contain it. However, the step of adding the inorganic salt to the immersion is preferably carried out after the lapse of a predetermined period from the start of the aerobic activation treatment. Specifically, the aerobic activation treatment is conducted while the immersion of the brewer's yeast is stirred at a predetermined temperature, and continuously, the inorganic salt is added to the yeast immersion at the point a predetermined time has passed. The predetermined time may vary depending various parameters associated with the activation treatment, but is approximately 2–20 hours.

The aerobatic activation treatment step according to this invention comprises stirring the immersion of the brewer's yeast under aeration conditions at a predetermined temperature. Suitable aeration conditions may be in the range of from 0.5 to 1 VVM (VVM: minutely airflow liter per liter of reaction volume) as expressed in terms of the quantity of airflow, but not limited thereto. The predetermined temperature may be selected such that it is a temperature suitable for the brewer's yeast in use to accumulate ribonucleic acid in the cell and it is normally in the range of from 30 to 50° C. If this temperature is below 10° C. or exceeds 30° C., the activity of the brewer's yeast will be lowered in the activation treatment step, which is not preferable. The treatment time may also be selected such that it is a time sufficient for the brewer's yeast in use to accumulate ribonucleic acid in the cell. The time may vary depending on the medium to be used or other treatment conditions. The activation treatment is preferably done at the aforementioned temperature for a period in the range of normally 5–24 hours.

When the treatment temperature, time and others are optimized and the compositional ingredients of the medium are adjusted in the aerobatic activation treatment step as described above, the activation treatment is feasible without substantially proliferating the brewer's yeast. Thus, 10% by weight of ribonucleic acid based on the weight of the cell body is produced in the brewer's yeast cell body. However, as described previously once the proliferation of the yeast cells starts and progresses, ribonucleic acid is consumed and its content decreases. It is, therefore, preferred that the yeast cell body be recovered before the ribonucleic acid has been consumed, that is, at the point the content of ribonucleic acid reaches a peak.

In order to identify the timing of yeast recovery, the present inventors determined to regard the point as the time required from the start of activation treatment that the content of ribonucleic acid reached a peak. The treatment time as described above (i.e., 5–24 hours) is data deduced from the results. At the point the treatment time has elapsed from the start of activation treatment, the yeast cell body is to be recovered from the immersion.

The recovery of the brewer's yeast cell body can be performed according to techniques known in the art. Suitable means, for example, include conventional techniques such as centrifugation, filtration and precipitation. According to this invention, recovery techniques known in the art can be combined with the aerobic activation treatment step to recover the brewer's yeast cell body containing 10% or more by weight of ribonucleic acid based on the weight of the cell body.

Further, the ribonucleic acid can be separated from the recovered brewer's yeast cell body by extraction (chemical method). As an alternative method there are known a biochemical method by which the yeast cells are decomposed by a lytic enzyme or the like and a physical method by which the cell body is disrupted using ultrasonic wave or the like. A suitable separation method may be selected in consideration of the separation efficiency and the utility of the ribonucleic acid. The obtained ribonucleic acid can be a raw material for a dietary supplement or a flavoring enhancer.

EXAMPLES

The invention will be described in greater detail by way of examples hereafter; however, these examples are in no way limitative on the invention In practicing the invention, both methods of a batch system and a flow system may be used in a similar manner to a conventional fermentation technique. The following examples employed the batch system.

Example 1

The recovered brewer's yeast (which was collected after beer production) was subjected to the treatment according to this invention in a batch system in a 30-L fermentation tank. The medium for use containing nutrient ingredients consisted of the following composition, for example: 400 g ammonium sulfate, 1620 g liquid sugar, 30 g $KH_2PO_4$, 200 g NaCl, 50 g yeast extract, 16 L water and other additives such as a defoaming agent.

The yeast recovered after beer production was washed by sieving and exchanging for fresh water, and centrifuged at 3000 rpm. The obtained yeast precipitate, 4 Kg, was added to the 30-L fermentation tank containing the medium. Under aeration the activation treatment of the yeast was carried out. The treatment conditions were a pH of 4.0, a temperature of 15° C., the quantity of airflow of 1 VVM and an agitation rate of 200 rpm; and the treatment continued for 7 hours. Subsequently, the yeast cell body was recovered by centrifugation. The yeast cell body was washed by exchanging for fresh water and heat-dried according to a conventional process for the production of dried yeast for foodstuff. The obtained yeast cell body (1 kg) was analyzed for its ribonucleic acid content according to the method of Schmidt, Tannhauser, and Schneider (STS method) (J. Biol. Chem. 164, 747 (1946)). Consequently, the content of ribonucleic acid was 12% based on the weight of the dried cell body and exceeded about three times that of the yeast cell body starting material. Sampling from the medium was carried out at appropriate intervals during the treatment described above; when the content of ribonucleic acid was determined similarly, it was found that the content increased gradually. The time-dependent change is shown in FIG. 1. The data shown in FIG. 1 enables the recovery timing of the yeast cell body to be determined. Specifically, if the conditions of activation treatment are substantially the same as those in the case of the present Example, it can be understood that the yeast cell body is adequately recovered from the immersion about 5 hours after the start of activation. Further, if collection is carried out about 6 to 7 hours after the start of activation, the yeast cell body the ribonucleic acid content of which is the highest (12% by weight) can be obtained. In addition, where the conditions of activation treatment are different, preliminary experiments for activation will be conducted under those conditions in advance and the time the ribonucleic acid content reaches 10% by weight or more, or the content reaches a peak will be measured in advance.

Example 2

Figure 2:
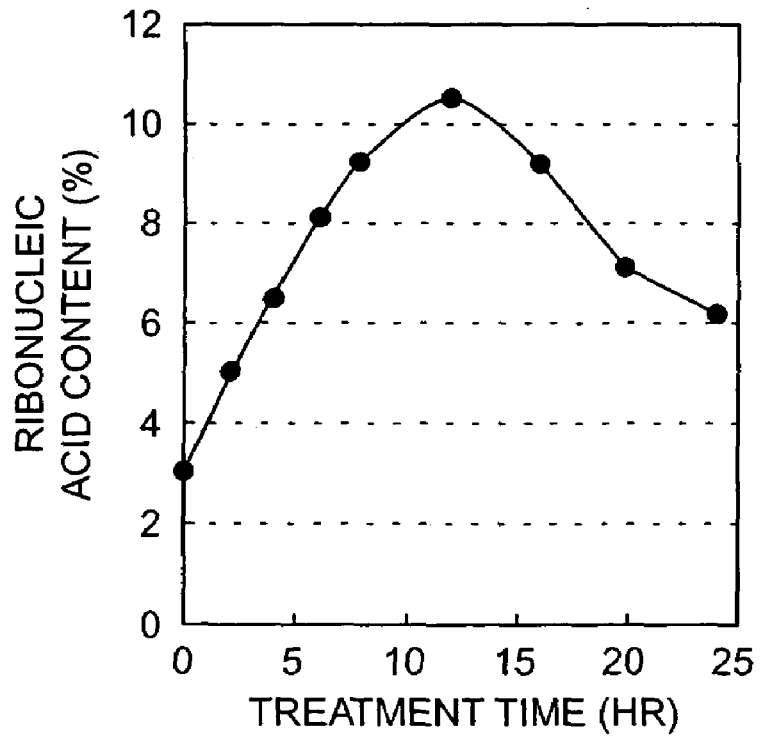
FIG. 2 is a graph showing the relationship between ribonucleic acid contents and brewer's yeast treatment time, where the treatment conditions are different from those in FIG. 1.

Following the method described in Example 1, the activation treatment was carried out under the identical conditions except that only the treatment temperature of yeast was changed from 15 to 19° C. Here, the treatment time was set to be as long as 24 hours, which exceeded 7 hours in Example 1. Sampling was conducted at 0, 2, 4, 6, 8, 12, 16, 20 and 24 hours after the start of treatment and the contents of ribonucleic acid were determined. As FIG. 2 shows, the content of ribonucleic acid increased in proportion to the treatment time with the peak of the content (exceeding 10% but less than 12%) appearing 12 hours later, but showed the tendency to decrease thereafter. Therefore, the level of the increase of ribonucleic cid in weight was lowered at a treatment temperature of 10° C. relative to the 15° C. used in Example 1. The content of ribonucleic acid at the peak point reached greater than about three times that at the start of treatment. The timing for recovery under these conditions is such that the content is 10% by weight or more and approximately 10 to 14 hours later.

Example 3

Figure 3:
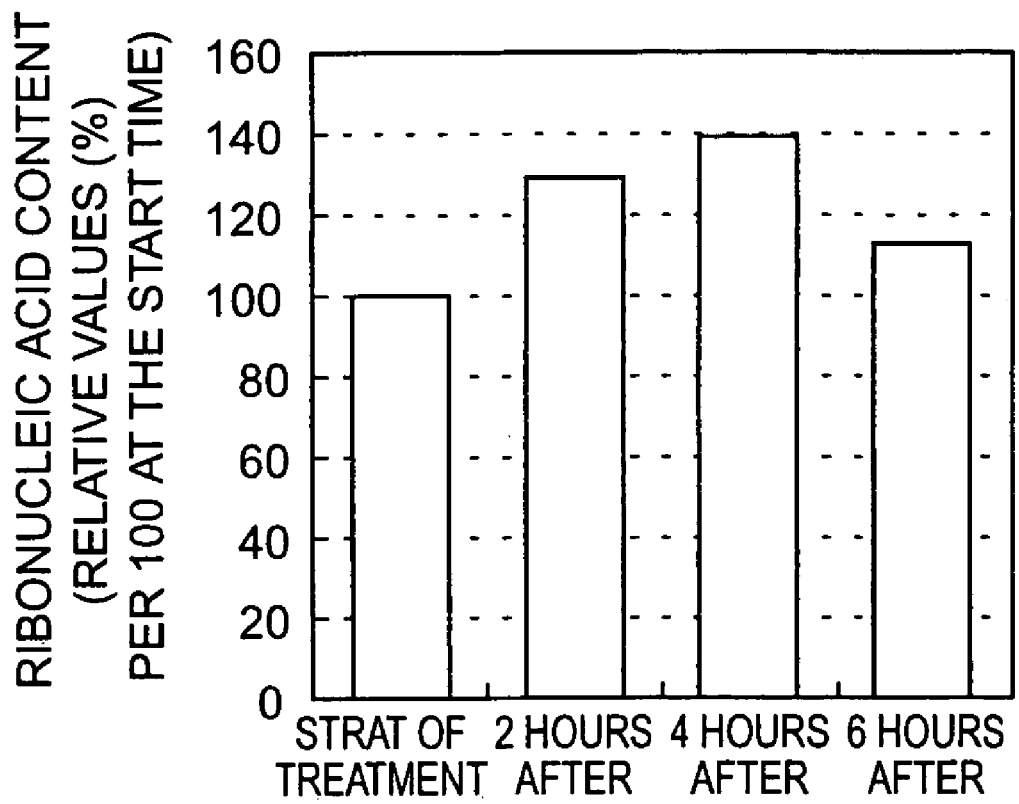
FIG. 3 is a bar graph showing the effects on the ribonucleic acid content of the timing of sodium chloride addition in the step of activation treatment of yeast.

The media similar to that used in Example 1 were prepared in different types, but none of them contained NaCl (sodium chloride). NaCl (200 g) was added to the media after the lapses of predetermined times from the start of treatment and the activation treatment of yeast was carried out on the respective media according to the method described in Example 1. The timing of NaCl addition was set at 2, 4, and 6 hours after the start of treatment. The contents of ribonucleic acid for the dried yeast cell bodies recovered from the respective lots were determined and plotted in FIG. 3. The content of ribonucleic acid was highest in the lot where NaCl was added 4 hours after the start of treatment and it was increased by about 40% compared to the case where NaCl was added at the time of start (Example 1). Accordingly, it has become apparent that the content of ribonucleic acid can be enhanced more by establishing the timing of NaCl addition as appropriate.

INDUSTRIAL APPLICABILITY

According to this invention, it will be possible to produce a yeast cell body containing a high ribonucleic acid content from brewer's yeast (particularly, from the recovered yeast after beer production). Therefore, such yeast cell bodies with high ribonucleic acid contents can be provided on an industrial scale.

Moreover, in the method of this invention, the ribonucleic acid content of the brewer's yeast cell body can be enhanced more by controlling the timing of addition of an inorganic salt.

The invention claimed is:

1. A method for producing a brewer's yeast cell body containing a high ribonucleic acid content comprising 10% by weight or more of ribonucleic acid based on the weight of the cell body, the method comprising:
   using a medium containing an ingredient for activating the brewer's yeast;
   immersing the brewer's yeast cell body in the medium in the presence of 0.5 to 2.0% by weight of an added inorganic salt; and
   stirring the immersion at a predetermined temperature to concurrently carry out an aerobic activation treatment,
   wherein the inorganic salt is an inorganic salt of a metal selected from an alkali metal, an alkaline earth metal or a transition metal.

2. A method for producing a brewer's yeast cell body containing a high ribonucleic acid content comprising 10% by weight or more of ribonucleic acid based on the weight of the cell body, the method comprising:

using a medium containing an ingredient for activating the brewer's yeast;

immersing the brewer's yeast cell body in the medium in the presence of an added inorganic salt; and stirring the immersion at a predetermined temperature to concurrently carry out an aerobic activation treatment, wherein the inorganic salt is sodium chloride.

3. The method for producing a brewer's yeast cell body containing a high ribonucleic acid content according to claim 1, wherein the step of adding an inorganic salt to the immersion is carried out prior to the start of the aerobic activation treatment.

4. The method for producing a brewer's yeast cell body containing a high ribonucleic acid content according to claim 1, wherein the step of adding an inorganic salt to the immersion is carried out after the lapse of a predetermined period from the start of the aerobic activation treatment.

5. The method for producing a brewer's yeast cell body containing a high ribonucleic acid content according to claim 1, wherein the predetermined temperature is in the range of from 10 to 30° C.

6. The method for producing a brewer's yeast cell body containing a high ribonucleic acid content according to claim 2, wherein the step of adding an inorganic salt to the immersion is carried out prior to the start of the aerobic activation treatment.

7. The method for producing a brewer's yeast cell body containing a high ribonucleic acid content according to claim 2, wherein the step of adding an inorganic salt to the immersion is carried out after the lapse of a predetermined period from the start of the aerobic activation treatment.

8. The method for producing a brewer's yeast cell body containing a high ribonucleic acid content according to claim 2, wherein the predetermined temperature is in the range of from 10 to 30° C.

9. The method for producing a brewer's yeast cell body containing a high ribonucleic acid content according to claim 2, wherein the brewer's yeast cell body is immersed in the medium in the presence of 0.5 to 2.0% by weight of added sodium chloride.

* * * * *